United States Patent [19]

Bourcier

[11] Patent Number: 4,534,940
[45] Date of Patent: Aug. 13, 1985

[54] ATOMIC ABSORPTION SPECTROPHOTOMETRIC MEASUREMENT OF MERCURY

[75] Inventor: Denis R. Bourcier, Logan, Utah

[73] Assignee: Utah State University Foundation, Logan, Utah

[21] Appl. No.: 362,501

[22] Filed: Mar. 26, 1982

[51] Int. Cl.$^3$ ............................................. G01N 21/31
[52] U.S. Cl. ....................................... 422/68; 356/311
[58] Field of Search ...................... 436/81, 164, 171; 422/68, 102; 356/437, 440, 311, 312

[56] References Cited

FOREIGN PATENT DOCUMENTS 1298978 12/1972 United Kingdom ................ 356/311

OTHER PUBLICATIONS

Siemer, Analytical Chem., 1980, 52, pp. 105–108.
M. C. Battigelli, "Mercury Toxicity from Industrial Exposure: A Critical Review of the Literature-Part II," 2 *J. Occup. Med.*, 337, (1960).
R. G. Smith, A. J. Vorwald, L. S. Patil, and T. F. Mooney, "Effects of Exposure of Mercury in the Manufacture of Chlorine," 31 *Am. Ind. Hyg. Assoc. J.*, 687, (1970).
G. M. Cherian, J. B. Hursh, T. W. Clarkson, and J. Allen, "Radioactive Mercury Distribution in Biological Fluids and Excretion in Human Subjects after Inhalation of Mercury Vapor," 33 *Arch. Environ. Health*, 109, (1978).
W. Stopford, S. C. Bundy, L. J. Goldwater, and J. A. Bittokofer, "Microenvironmental Exposure to Mercury Vapor", 39 *Am. Ind. Hyg. Assoc.*, 378, (1978).
J. F. Uthe, F. A. J. Armstrong, and M. P. Stainton, "Mercury Determination in Fish Samples by Wet Digestion and Flameless Atomic Absorption Spectrophotometry," 27 *J. Fish. Res. Bd. Canada*, 805, (1970).
S. Tong, "Stationary Cold Vapor Atomic Absorption Method for Mercury Determination," 50, *Anal. Chem.*, 412, (1978).
A. M. Ure, "The Determination of Mercury by Non–Flame Atomic Absorption and Fluorescence Spectrometry-A Review", 76 *Anal. Chim. Acta.*, 1, (1975).
A. A. Koch and D. C. Manning, "Non-Flame Methods for Mercury Determination by Atomic Absorption: A Review," *Mercury in the Western Environment*, Workshop Proceedings, Oregon State University, (Feb. 25–26, 1971).
F. A. J. Armstrong and J. F. Uthe, "Semi-Automated Determination of Mercury and Fish Tissue," *Mercury in the Western Environment*, Workshop Proceedings, Oregon State University, 243, (Feb. 25–26, 1971).
R. R. Claeys, "Introduction to the Analytical Methods for the Determination of Mercury Compounds," *Mercury in the Western Environment*, Workshop Proceedings, 229, (Feb. 24–26, 1971).

*Primary Examiner*—Hiram H. Bernstein
*Attorney, Agent, or Firm*—Workman, Nydegger & Jensen

[57] ABSTRACT

An apparatus and method for atomic absorption spectrophotometric measurement of submicrogram amounts of mercury utilizing a combined absorption-reduction cell sized to fit within the absorption compartment of a standard spectrophotometer. The absorption-reduction cell comprises an absorption chamber which is generally cylindrical in shape and a mixing chamber connected to the lower portion of the absorption chamber into which the sample to be analyzed and a reductant are added. The cell also includes an inlet port, and outlet port, and an air intake port used to flush and clean the cell after use.

15 Claims, 3 Drawing Figures

ATOMIC ABSORPTION SPECTROPHOTOMETRIC MEASUREMENT OF MERCURY

BACKGROUND

1. The Field of the Invention

The present invention relates to an apparatus and method for the measurement of submicrogram amounts of mercury by flameless atomic absorption spectrophotometry; more particularly, the invention relates to a one piece mercury absorption-reduction cell which can be fitted within the absorption chamber of an atomic absorption spectrophotometer.

2. The Prior Art

Science has long recognized the toxicity of mercury and that mercury can be taken into the body through the food we eat, the water we drink or even the air we breathe. Although man and animals are rarely exposed to mercury in concentrations great enough to cause immediate physical effects, mercury accumulates within the body until it reaches toxic levels.

Unfortunately, modern technology and industrial operations have increased the potential for exposure to mercury because many manufacturing processes emit mercury vapors into the working environment. For decades, the literature has contained reviews of the toxic effects of industrial exposure to mercury. See M. C. Battigelli, "Mercury Toxicity from Industrial Exposure: A Critical Review of the Literature—Part II, " 2 *J. Occup. Med.* 337 (1960); R. G. Smith, A. J. Vorwald, L. S. Patil, and T. F. Mooney, "Effects of Exposure of Mercury in the Manufacture of Chlorine," 31 *Am. Ind. Hyg. Assoc. J.* 687 (1970). In light of the dangers of mercury poisoning, much attention has been directed to the development of methods for measuring mercury concentrations in the human body.

Today, there is general agreement that blood mercury levels can be used as an estimate of the recent exposure and that the amount of mercury in the urine can be an indicator of mercury accumulation in the kidney. See G. M. Cherian, J. B. Hursh, T. W. Clarkson, and J. Allen, "Radioactive Mercury Distribution in Biological Fluids and Excretion in Human Subjects after Inhalation of Mercury Vapor," 33 *Arch. Environ. Health* 109 (1978). It has been found that by monitoring mercury levels in urine at the end of each work week, it is possible to ascertain mercury exposure of employees exposed to mercury vapors during the previous week. See W. Stopford, S. D. Bundy, L. J. Goldwater, and J. A. Bittikofer, "Microenvironmental Exposure to Mercury Vapor," 39 *Am. Ind. Hyg. Assoc. J.* 378 (1978). Hence, many industries where there is potential for mercury exposure have initiated screening techniques as a means of protecting their employees. However, in order to obtain meaningful information at a reasonable expense, these industries require an accurate, yet quick, method for monitoring mercury levels in blood and urine samples.

While several methods for determining trace amounts of mercury have been developed, the generally accepted and most widely used method was developed in 1970 by Uthe et al. and comprises a complicated apparatus which is used in conjunction with an atomic absorption spectrophotometer. See J. F. Uthe, F. A. J. Armstrong and M. P. Stainton, "Mercury Determination in Fish Samples by Wet Digestion and Flameless Atomic Absorption Spectrophotometry, 27 *J. Fish. Res. Bd. Canada* 805 (1970). The basis of this NIOSH-approved procedure rests in the ability of mercury to be reduced in solution to its elemental state by the addition of a reductant, typically a stannous salt such as stannous sulfate. The mercury in the vapor phase is then swept from the air space above the solution into a cell located in the absorption compartment of an atomic absorption spectrophotometer. The absorbance of mercury at 253.7 nm is then measured as a function of the concentration of mercury in the sample.

The relationship between the mercury concentration and the light absorption is generally established by one of two methods. For the first method, a set of samples of different known concentrations of mercury are run through the system. The absorbance for each sample is noted, and a callibration curve can then be easily prepared in order to correlate absorbancy to mercury concentration. The second method utilizes the process of standard additions to determine the amount of mercury in a sample.

A common embodiment of the Uthe apparatus (which is generally depicted in FIG. 1) basically consists of a reduction chamber which is usually in the form of a flask into which a sample of 25 ml or more is introduced. A reductant is then added to the sample and the mixture is thoroughly mixed with a magnetic stirrer for several minutes. Air is then forced through the reduction chamber to sweep the mercury laden gases into a second chamber located in the absorption compartment of an atomic absorption spectrophotometer.

A modified version of the Uthe apparatus replaces the magnetic stirrer with a bubbler inserted into the sample. The bubbler provides the dual service of mixing the sample and reductant and also providing the air to force the mercury laden vapors into the absorption chamber.

The absorption chamber of the Uthe apparatus is generally a cuvette with quartz lenses located on the ends. The concentration of the mercury in the vapor is then measured, and the gases are vented to a scrubber. Usually, a dessicant tube is located between the reduction and absorption chambers to remove water vapors so that they do not fog the absorption compartment, thereby creating erroneous results. Alternatively, the absorption chamber may be sufficiently heated to prevent fog formation.

The Uthe prior art apparatus has greatly improved the ability to obtain the sensitivity needed to detect trace amounts of mercury. However, there are several disadvantages and problems associated with the apparatus. First, a relatively large sample (i.e., 25 ml or more) is typically needed to perform the measurement. Normally, 25 ml is the total amount of sample which is available from a single digest. Thus, it is difficult, if not impossible, to perform repetitive tests to verify the data obtained by the Uthe method. Moreover, in many applications, the Uthe method is very impractical because the specimen sizes are often so small (such as with atmospheric fallout and tissues from small animals) that a suitable sample cannot be prepared.

Second, the Uthe apparatus requires positive pressure to sweep the mercury laden vapors from the mixing flask to the cuvette. Accordingly, if there are any leaks within the system, this positive pressure will force the toxic mercury vapors into the atmosphere, thereby subjecting the laboratory technician performing the measurements to the toxic mercury vapors.

Third, mercury is often absorbed onto the walls of the complicated apparatus and the extensive tubing connecting the flask and cuvette, thereby resulting in erroneous readings. Moreover, the mercury build up on the tubing creates problems in properly cleaning the apparatus, as well as reducing the number of tests which can be conducted in a given period of time.

In addition to these significant problems, the prior art Uthe apparatus is relatively expensive and occupies a significant amount of space in front of or on the side of the atomic absorption spectrophotometer. These problems have thus caused those skilled in the art to seek after better systems for analyzing trace amounts of mercury.

A method somewhat simpler than that of Uthe was described in S. Tong, "Stationery Cold Vapor Atomic Absorption Method For Mercury Determination," 50 Anal. Chem. 412 (1978). The Tong method utilizes a 4 cm ultraviolet ("UV") cell. According to this method, both the sample and the reductant are mixed together within the UV cell. The cell is then placed within the atomic absorption spectrophotometer and the mercury concentration in the air space of the cell is measured.

This procedure also has several drawbacks. First, the UV cell must be removed from the spectrophotometer between samples to be cleaned and reloaded. The cell must be aligned within the light path of the spectrophotometer for every sample. Also, small droplets of the solution typically adhere to the quartz lenses on the ends of the cuvette, thereby interfering with the absorption reading.

In view of the foregoing, it would be a significant advancement in the art to provide an apparatus and method for measuring trace amounts of mercury in which measurements can be made on small samples so that replicate data can be taken with respect to a single digest. It would also be advantageous to provide an apparatus which is simple to use and easy to clean. A further advancement in the art would be to provide an apparatus which does not require the use of positive pressures with the attendant possibility of leaks which could contaminate the area in which the technician operates. Such an invention is disclosed and claimed herein.

BRIEF SUMMARY AND OBJECTS OF THE INVENTION

An apparatus and method are provided for rapid, accurate measurement of submicrogram amounts of mercury by utilizing an atomic absorption spectrophotometer. The entire absorption-reduction cell is designed to be fitted within the absorption chamber of the atomic absorption spectrophotometer.

The apparatus includes a sample-reductant container which is fitted to the bottom of a cylindrical shaped absorption cell, with the absorption cell having quartz lenses cemented to the ends thereof. Ports are located within the apparatus for air intake, sample removal, and for the introduction of the sample, the reductant, and a washing solution used in cleaning. An air, water, or vacuum driven magnetic stirrer is positioned below the sample container in order to provide mixing to insure proper reduction of the mercury in the sample. The apparatus is mountable on a holder which is fitted into the burner mount so that the absorption cell can be readily positioned and aligned within the absorption chamber of the spectrophotometer.

To perform a mercury measurement according to the present invention, an aliquot of suitably prepared digest is introduced into the sample container in the absorption cell, and a reductant solution is then added. The mixture is then mixed within the sample-reductant container, and after about three minutes, the peak absorbance of mercury at 253.7 nm is noted and preferably recorded by a chart recorder connected to the spectrophotometer.

After measurement, a vacuum connected to the sample removal port withdraws the sample and mercury laden vapors from the cell under negative pressure. The absorption cell can then be readily cleaned preparatory to the next measurement. The entire process takes only about four minutes.

It is therefore, a primary object of the present invention to provide an improved apparatus and method for measuring trace amounts of mercury which is simple to use and results in accurate, reproducible measurements.

It is a further object of the present invention to provide an apparatus and method for measuring trace amounts of mercury which only requires the use of small amounts of the sample in each measurement.

Another object of the present invention is to provide an apparatus and method for measurement of trace amounts of mercury which minimizes the dangers of leakage and contamination to the technician.

A still further object of the present invention is to provide an apparatus and method for measuring trace amounts of mercury which can be adapted to fit within the compartment of most standard atomic absorption spectrophotometers.

These and other objects and features of the present invention will become more fully apparent from the following description and appended claims taken in conjunction with the accompanying drawings.

BRIEF DESCRIPTIONS OF THE DRAWINGS

DETAILED DESCRIPTION OF THE PREFERRED EMBODIMENT

The present invention relates to a new and improved apparatus and method for cold vapor measurements of submicrogram amounts of mercury using an atomic absorption spectrophotometer. The present invention is an improvement over the prior art device in that it provides an apparatus which is compact and adapted to fit completely within the absorption chamber of a standard atomic absorption spectrophotometer. The apparatus does not use positive pressure to transport the mercury vapors, thereby eliminating the possibility of leakage and contamination which exists with the prior art devices. Also, only a 1–5 milliliter aliquot of the sample is required for each measurement, thus allowing for repetitive tests on a single sample.

Although the apparatus and method of the present invention can be used for numerous applications, it has been found to be particularly effective for measuring mercury concentrations in blood and urine. The apparatus of the present inention is particularly adaptable for use in screening persons working in an industrial environment with potential exposure to mercury vapors. In light of the versatility of the present invention, it is also useful in measuring mercury concentrations in water supplies and in biological samples, such as liver and kidney samples.

Figure 2:
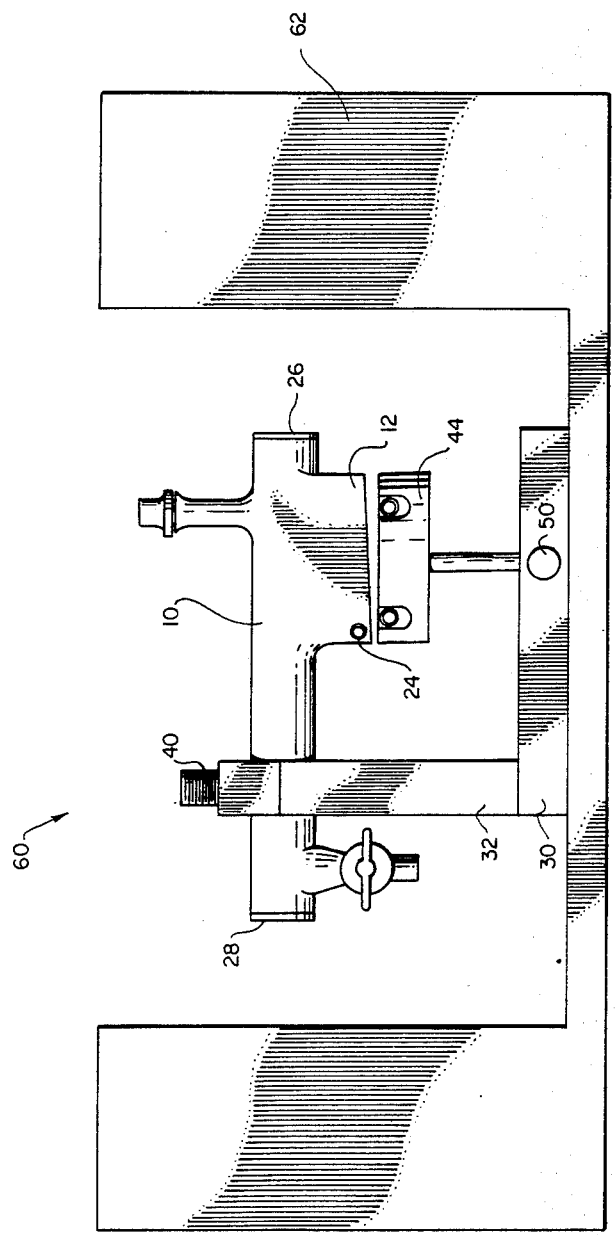
FIG. 2 is a schematic representation of a preferred embodiment of the present invention within the absorption compartment of an atomic absorption spectrophotometer.
Figure 3:
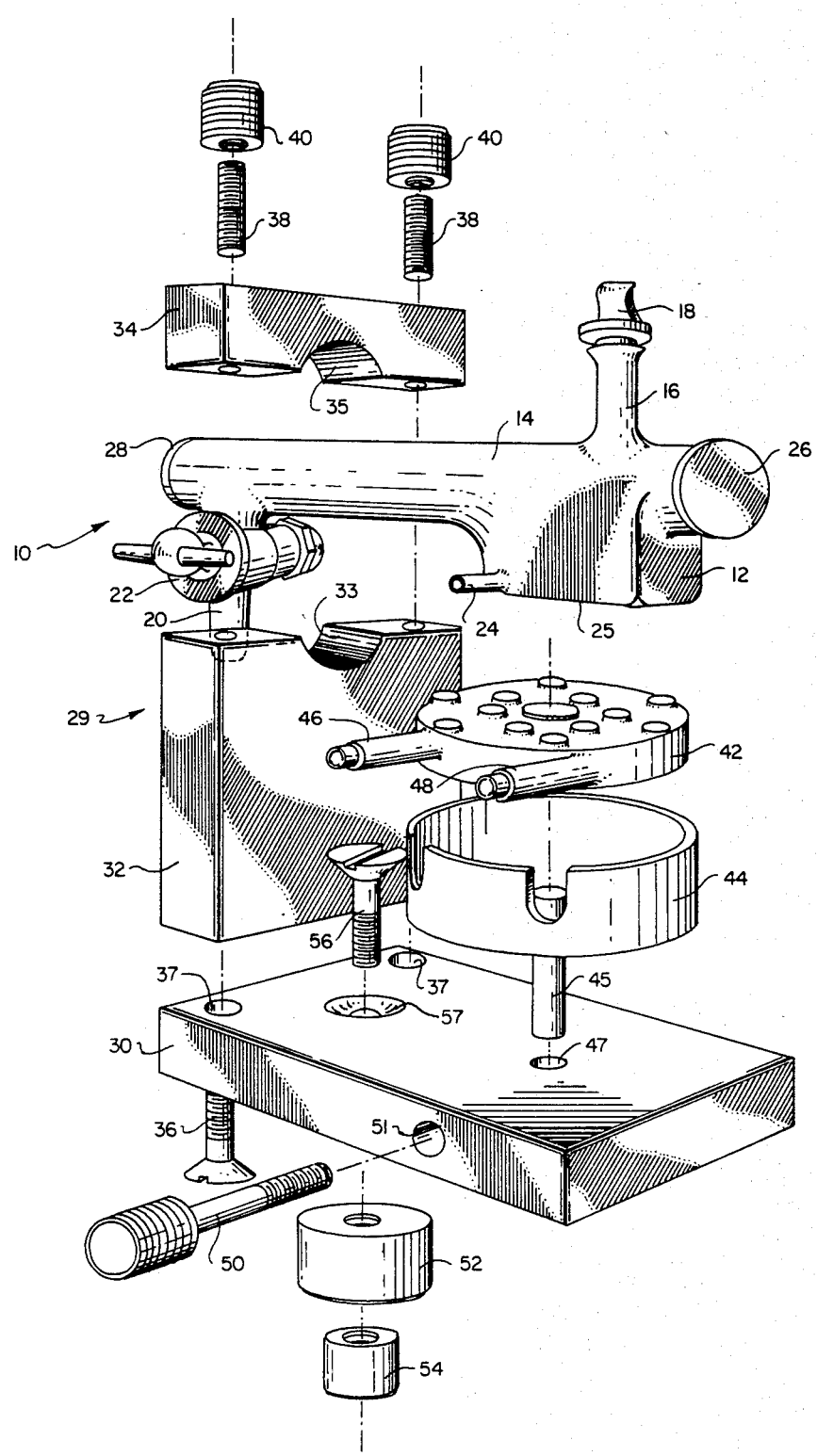
FIG. 3 is an exploded perspective view of a preferred embodiment of the present invention and a bracket for mounting it to the burner mount of a typical atomic absorption spectrophotometer.

The preferred embodiment of the present invention can best be understood by reference to FIGS. 2 and 3 where like parts are designated by like numerals. FIGS. 2 and 3 illustrate the preferred embodiment of the absorption-reduction cell used in the present invention to determine submicrogram amounts of mercury by a stationary cold-vapor technique. With specific reference to FIG. 2, the absorption-reduction cell, generally designated 10, is shown in the absorption compartment 60 of a standard atomic absorption spectrophotometer 62.

As best illustrated in the exploded perspective view of FIG. 3, absorption cell 10 is basically comprised of a sample-reductant mixing chamber 12 and an absorption chamber 14. Located on the top of absorption chamber 14 is inlet port 16 which is selectively sealable by stopper 18. Cell 10 also has an air intake port 20 which is selectively opened and closed by stopcock 22.

Sample removal port 24 is located in the bottom of mixing chamber 12. A piece of tubing (not shown) connects sample removal port 24 to a vacuum line capable of evacuating cell 10. The tubing is clamped off while the cell is in use. In the preferred embodiment, a bottom portion 25 of mixing chamber 12 is slightly inclined downwardly towards removal port 24 to insure that all of the sample can be readily removed from the absorption-reduction cell.

Quartz lenses 26 and 28 are attached to the ends of absorption chamber 14 in order to allow for clear passage of the light rays through the absorption chamber.

In the preferred embodiment, the absorption chamber is approximately 12 cm is length and has a diameter of about 2 cm. The mixing chamber is designed to hold about 9 ml. Of course, it will be readily appreciated that other sizes can be used for the cell without significantly affecting the sensitivity of the apparatus. In fact, an absorption cell 16 cm long and 2.5 cm in diameter has been tested, and it was found to give comparable results.

Cell 10 is clamped in mounting unit 29 for positioning within the spectrophotometer. Mounting unit 29 generally comprises base place 30, lower cell bracket 32, and upper cell bracket 34. Lower cell bracket 32 is mounted on top of base plate 30 by mounting screws 36 which extend through holes 37 of base plate 30. In the preferred embodiment, the entire unit can be assembled and positioned in the spectrophotometer in a manner of minutes, and there is no need to remove the apparatus between measurements. In fact, the cell can be cleaned and prepared for with a new sample without removing the apparatus from its mount.

When assembled, a portion of absorption chamber 14 is positioned within groove 33 in the top of lower cell bracket 32, and then upper cell bracket 34 is positioned with groove 35 partially encircling one end of the absorption chamber. Lower cell bracket 32 and upper cell bracket 34 may then be suitably held in a fixed position by retainer screws 38 and finger bolts 40.

Mounting nuts 52 or 54 may be secured to the bottom of base plate 30 by mounting screw 56 which extends through hole 57 in base plate 30. Mounting nuts 52 and 54 are sized to fit within the holes in the burner mounts of all of the common models of generally available atomic absorption spectrophotometers.

When attempting to make mercury concentration determinations, it is essential that the sample and reductant are thoroughly mixed in the sample-reductant mixing chamber. In order to assure thorough mixing, magnetic stirrer 42 is provided such that it is positioned on top of base plate 30 and directly below mixing chamber 12.

In the preferred embodiment, magnetic stirrer 42 is either water, air, or vacuum propelled. Inlet port 46 and outlet port 48 are connected to the appropriate water, air, or vacuum sources to drive magnetic stirrer 42. Magnetic stirrer 42 is mounted within holder 44 which is secured to base plate 30.

In order to properly position the magnetic stirrer in relation to the sample-reductant chamber, magnetic stirrer holder pin 45 is located on the bottom of holder 44 and is inserted into hole 47 of base plate 30 such that holder adjustment knob 50 is screwed into hole 51 and comes into engagement with holder pin 45 to secure holder 40 in place. Any generally available and suitably sized magnetic stirring rod (not shown) can be positioned within mixing chamber 12 to mix the sample and reductant.

As will be seen from the following discussion, the method of operation of the present invention allows for rapid, yet accurate, measurements of the levels of mercury in the samples. A sample can be prepared for testing by a variety of well-recognized methods. One method involves adding about 3 ml of urine or about 2 ml of blood to about 3 ml of a mixture of about 20% nitric acid ($HNO_3$) and about 80% sulfuric acid ($H_2SO_4$). The solution is then heated for two hours at 58° C. in a shaking water bath. The solution is cooled on ice and about 3 ml of 5% potassium permanganate and about 2 ml of 5% potassium persulfate are added. This mixture, called a digest, is then heated for two hours in a water bath at 95° C. Afterwards, the digest is cooled at room temperature, transferred to a 25 ml volumetric flask and diluted to volume with distilled-deionized water.

There are several additional standard methods normally used in the industry to prepare digests and any one is acceptable. A review of many of the accepted methods is contained in A. M. Ure, "The Determination of Mercury by Non-flame Atomic Absorption and Fluorescence Spectrometry—A Review." 76 *Anal. Chem.* 1 (1975), and A. A. Koch and D. C. Manning, "Mercury in the Western Environment," D. R. Buhler (Ed.), *Continuing Education Publications, Oregon State University,* 234 (1971).

A thoroughly cleaned absorption cell 10 is placed in mounting unit 29 which is positioned in the absorption chamber of the spectrophotometer. The burner mount horizontal and vertical adjustment knobs on the spectrophotometer are used to position the absorption-reduction cell in the light path in the absorption chamber.

Once the unit is in place within the spectrophotometer, the technician can begin the analysis sequence. Stopper 18 is removed from inlet port 16 and an aliquot of from about one to about five milliliters of the sample to be tested is pipetted into mixing chamber 12. Approximately 1 ml of a reductant, such as stannous sulfate, is also pipetted into the mixing chamber through the inlet port and stopper 18 is replaced.

A clamp on the vacuum hose connected to outlet port 48 on magnetic stirrer 42 is removed allowing the stirrer to spin and thoroughly mix the sample and reductant within mixing chamber 12. In the preferred embodiment, magnetic stirrer 42 is vacuum propelled, since vacuum has been found to provide a more stable speed. The reproducibility of the measurements depends in part on the mixing which occurs. Thus, the constant mixing speed provided by a vacuum eliminates one possible source of error. Therefore, outlet port 48 is preferably connected to a vacuum source, and inlet port 46 is vented to the atmosphere.

After about three minutes, the mercury has been reduced to its elemental state, and the peak absorbance can be noted or recorded on a strip chart recorder connected to the spectrophotometer. The clamp on the vacuum hose on the magnetic stirrer is then replaced.

Stopcock 22 on air intake port 20 is then turned providing an open passage for air to enter cell 10, and the clamp on the hose connected to sample removal port 24 is removed in order to allow the sample to be flushed from the cell and into a waste flask containing a suitable reagent such as a mixture of 0.1M potassium permanganate ($KMnO_4$) and 10% sulfuric acid ($H_2SO_4$) which reacts with the mercury to prevent contamination of the surroundings.

A small amount of wash solution (as little as 5–10 ml) consisting of, for example, a 10% concentrated nitric acid solution is then pipetted into the system through inlet port 16 and flushed out to clean the cell and prepare it for the next sample. The air intake and sample removal ports are then sealed and the apparatus is ready for the next sample.

The entire testing and cleaning procedure takes only about 4 minutes. Therefore, a trained technician can perform approximately 15 analyses in an hour. This is especially valuable in industrial screening programs where a great number of samples must be run on a regular basis.

Tests have been performed to determine the sensitivity of the apparatus and method of the present invention. It has been found that the system will accurately detect amounts of mercury as small as 1 ng ($10^{-9}$ grams). If a 5 ml sample is used, this correlates to a 0.2 ng/ml sensitivity.

Tests were also performed to determine the reproducibility of the results. In one study, samples containing 4.0, 20.0, and 80.0 ng of mercury were tested. The coefficients of variation for 10 samples of each concentration were 4.7%, 1.5%, and 1.6% respectively. In light of the amounts being measured, these coefficients of variation are believed to be excellent and at least as reproducible, if not better, than that achieved by prior art devices.

Figure 1:
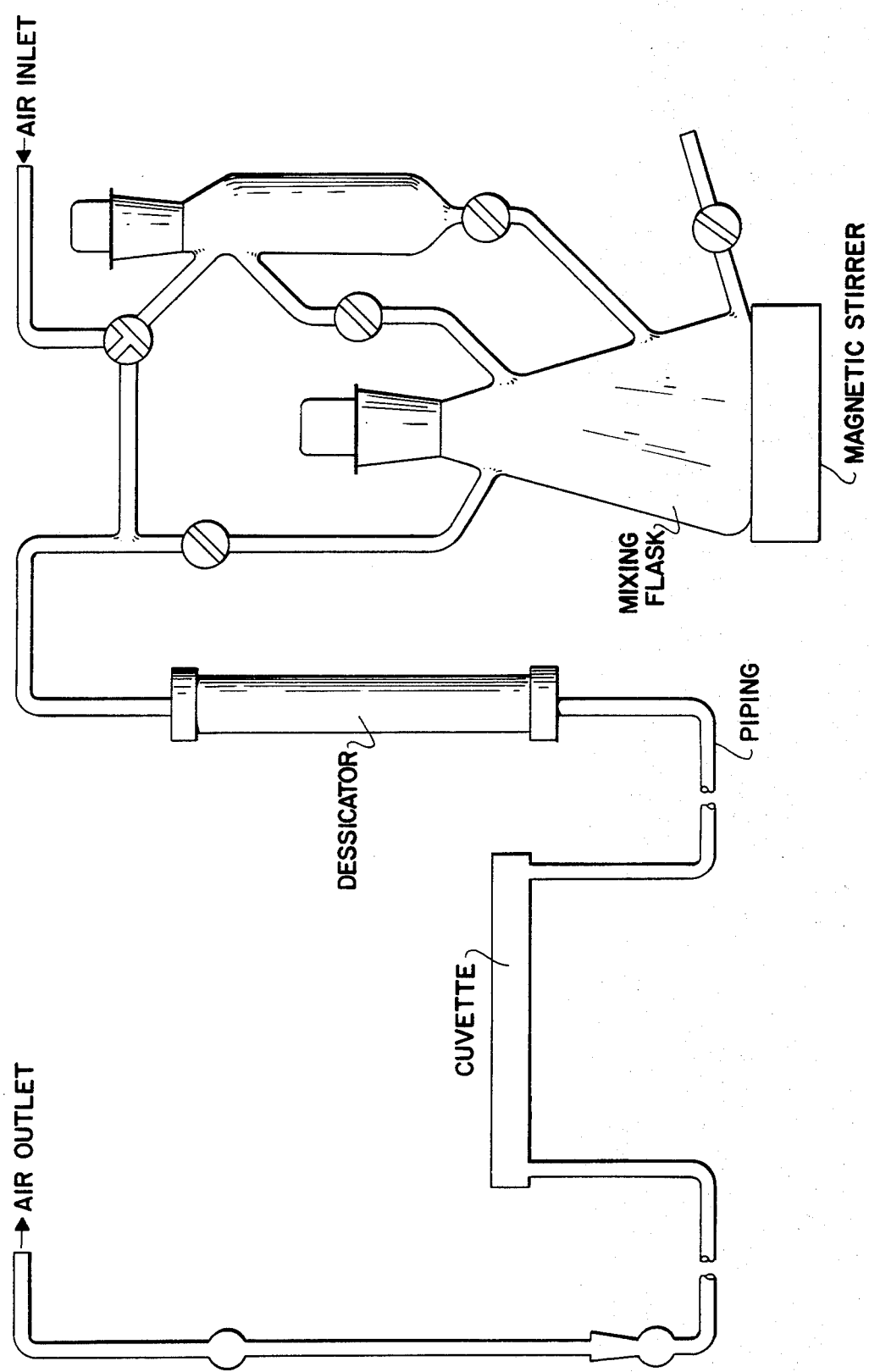
FIG. 1 is a schematic representation of the prior art Uthe apparatus.

The advantages of the present invention can best be understood by comparison to the prior art apparatus of Uthe et al. which is generally illustrated in FIG. 1. The apparatus of the present invention differs from the prior art in that the present invention is completely contained within the absorption chamber of a spectrophotometer, thereby removing the inconvenience and danger of having a complicated, glassware system in front of or near the side of the spectrophotometer. The unique combination of the mixing chamber and the absorption chamber in a single unit allows for measurements to be taken on samples of from about one to about five milliliters instead of twenty to twenty five milliliters or more which is required by the Uthe device. Also, since the mixing chamber is directly attached to the absorption chamber, piping connecting the two is eliminated, thereby eliminating large amounts of surface area which can adsorb mercury vapors and cause inaccurate readings as well as make cleaning very difficult. Another advantage of the present invention, is that positive pressure is not used to force the mercury vapors from the mixing chamber into the absorption chamber. This eliminates the possibility of having mercury vapor escape through leaks and contaminating the atmosphere surrounding the technician performing the measurements. Indeed, the suction system of the present invention functions to prevent leaks to the outside environment.

Although the present invention is designed to be used with a standard atomic absorption spectrophotometer, its use is not so limited. It will be readily appreciated that the present invention can also be used in commercial mercury detection units which utilize atomic absorption techniques.

As will be readily appreciated, the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by United States Letters of Patent is:

1. An apparatus for measurement of mercury by an atomic absorption spectrophotometer, comprising:
    an absorption chamber adapted for use in the spectrophotometer;
    a mixing chamber adjacent and connected to the absorption chamber into which a sample to be analyzed and a reductant are added, said mixing chamber being integral with and forming a portion of the absorption chamber such that the mixing chamber and the absorption chamber are mountable within the absorption compartment of the spectrophotometer;
    an inlet port for introducing the sample and the reductant into the mixing chamber; and
    an outlet port for removal of the sample and the reductant from the mixing chamber, said outlet port being positioned such that negative pressure is used to remove the sample and the reductant after the measurement is completed;
    wherein samples may be added to and removed from said apparatus while said apparatus is mounted within the absorption compartment of the spectrophotometer such that multiple samples may be analyzed without the necessity of removing the apparatus from the absorption compartment of the spectrophotometer.

2. An apparatus for measurement of mercury as defined in claim 1 further comprising an air intake port for flushing the apparatus.

3. An apparatus for measurement of mercury as defined in claim 1 wherein the absorption chamber is cylindrical in shape and has quartz lenses attached to both ends.

4. An apparatus for measurement of mercury as defined in claim 1 wherein the mixing chamber is located on a lower portion of the absorption chamber.

5. An apparatus for measurement of mercury as defined in claim 1 wherein the mixing chamber is rectangular in shape.

6. An apparatus for measurement of mercury as defined in claim 5 wherein the mixing chamber extends along only about one third of the length of the absorption chamber.

7. An apparatus for measurement of mercury as defined in claim 1 further comprising means for stirring the contents of the mixing chamber while said apparatus is mounted within the absorption compartment of the spectrophotometer.

8. An apparatus for measurement of mercury as defined in claim 7 wherein said stirring means comprises a magnetic stirrer positioned below the mixing chamber.

9. An apparatus for measurement of submicrogram amounts of mercury using atomic absorption spectrophotometry, comprising:
   an absorption chamber with quartz lenses attached to the ends thereof adapted for use in an atomic absorption spectrophotometer;
   a mixing chamber adjacent to and extending along at least a portion of the bottom of the absorption chamber into which a simple to be analyzed and a reductant are added, said mixing chamber being integral with and forming a portion of the absorption chamber such that the mixing chamber and the absorption chamber are mountable within the absorption compartment of the spectrophotometer;
   an inlet port located in the top of the absorption chamber directly above the mixing chamber through which the sample and reductant are added;
   an outlet port located in a lower portion of the mixing chamber for removal of the sample and reductant from the mixing chamber, said outlet port being positioned such that negative pressure is used to remove the sample and the reductant after the measurement is completed;
   an air intake port located in the absorption chamber for flushing the apparatus;
   wherein samples may be added to and removed from said apparatus, and said apparatus may be cleaned, while said apparatus is mounted within the absorption compartment of the spectrophotometer such that multiple samples may be analyzed without the necessity of removing the apparatus from the absorption compartment of the spectrophotometer.

10. An apparatus for measurement of submicrogram amounts of mercury as defined in claim 9 wherein the absorption chamber is cylindrical in shape.

11. An apparatus for measurement of submicrogram amounts of mercury as defined in claim 9 wherein the mixing chamber extends along only about one third of the length of the absorption chamber.

12. An apparatus for measurement of submicrogram amounts of mercury as defined in claim 9 further comprising a magnetic stirrer positioned below the mixing chamber.

13. An apparatus for the measurement of submicrogram amounts of mercury as defined in claim 9 wherein the entire apparatus is sized to fit within the burner compartment of a standard spectrophotometer.

14. An apparatus for measurement of submicrogram amounts of mercury using atomic absorption spectrophotometry comprising:
   an absorption chamber having quartz lenses attached to the ends thereof adapted for use in an atomic absorption spectrophotometer;
   a mixing chamber adjacent to and extending along at least a portion of the bottom of the absorption chamber into which a sample to be analyzed and a reductant are added, said mixing chamber being integral with and forming a portion of the absorption chamber such that the mixing chamber and the absorption chamber are mountable within the absorption compartment of the spectrophotometer;
   an inlet port located in the top of the absorption chamber directly above the mixing chamber through which the sample and reductant are added;
   an outlet port located in a lower portion of the mixing chamber for removal of the sample and reductant from the mixing chamber, said outlet port being positioned such that negative pressure is used to remove the sample and the reductant after the measurement is completed;
   an air intake port located in the absorption chamber for flushing the apparatus;
   a means for stirring the contents of the mixing chamber while said apparatus is mounted within the absorption chamber of the spectophotometer;
   wherein samples may be added to and removed from said apparatus, and said apparatus may be cleaned, while said apparatus is mounted within the absorption compartment of the spectrophotometer such that multiple samples may be analyzed without the necessity of removing the apparatus from the absorption compartment of the spectrophotometer.

15. An apparatus for measurement of submicrogram amounts of mercury as defined in claim 14 wherein said stirring means comprises a magnetic stirrer positioned below the mixing chamber.

* * * * *

UNITED STATES PATENT AND TRADEMARK OFFICE
CERTIFICATE OF CORRECTION

PATENT NO. : 4,534,940

DATED : August 13, 1985

INVENTOR(S) : DENIS R. BOURCIER

It is certified that error appears in the above-identified patent and that said Letters Patent is hereby corrected as shown below:

```
Column 2, line 41, "dessicant" should be --desiccant--
Column 7, line 6, "vacuum" should be --a vacuum--
Column 8, line 6, "," should be deleted
Column 9, line 25, "simple" should be --sample--
```

Signed and Sealed this

Twelfth Day of November 1985

[SEAL]

Attest:

DONALD J. QUIGG

Attesting Officer

Commissioner of Patents and Trademarks